(12) United States Patent
Hung et al.

(10) Patent No.: US 8,615,308 B2
(45) Date of Patent: *Dec. 24, 2013

(54) HIGH DENSITY ARRAY OF MICRO-MACHINED ELECTRODES FOR NEURAL STIMULATION

(75) Inventors: Andy Hung, Irvine, CA (US); Robert Greenberg, Los Angeles, CA (US); Dau Min Zhou, Saugus, CA (US); Jack Judy, Los Angeles, CA (US); Neil Talbot, Montrose, CA (US)

(73) Assignee: Second Sight Medical Products, Inc., Sylmar, CA (US)

( * ) Notice: Subject to any disclaimer, the term of this patent is extended or adjusted under 35 U.S.C. 154(b) by 333 days.

This patent is subject to a terminal disclaimer.

(21) Appl. No.: 12/718,864

(22) Filed: Mar. 5, 2010

(65) Prior Publication Data

US 2010/0168830 A1    Jul. 1, 2010

Related U.S. Application Data

(60) Division of application No. 11/488,806, filed on Jul. 17, 2006, now Pat. No. 7,706,893, which is a continuation of application No. 10/160,468, filed on May 1, 2002, now Pat. No. 7,676,274.

(60) Provisional application No. 60/287,415, filed on May 1, 2001, provisional application No. 60/314,828, filed on Aug. 24, 2001.

(51) Int. Cl.
*A61N 1/04* (2006.01)

(52) U.S. Cl.
USPC .......................................... 607/116

(58) Field of Classification Search
USPC .......................................... 607/116
See application file for complete search history.

(56) References Cited

U.S. PATENT DOCUMENTS

| | | | |
|---|---|---|---|
| 3,755,704 A * | 8/1973 | Spindt et al. | 313/309 |
| 4,240,878 A | 12/1980 | Carter | |
| 4,750,977 A | 6/1988 | Marrese | |
| 4,953,387 A * | 9/1990 | Johnson et al. | 73/25.03 |
| 5,109,844 A | 5/1992 | de Juan, Jr. et al. | |
| 5,318,572 A * | 6/1994 | Helland et al. | 607/121 |
| 5,531,774 A | 7/1996 | Schulman et al. | |
| 5,935,155 A | 8/1999 | Humayun et al. | |
| 6,151,967 A * | 11/2000 | McIntosh et al. | 73/514.32 |
| 6,245,444 B1 * | 6/2001 | Marcus et al. | 428/616 |
| 6,400,989 B1 | 6/2002 | Eckmiller | |
| 6,458,157 B1 | 10/2002 | Suaning | |
| 7,259,508 B2 * | 8/2007 | Witmer | 313/475 |

* cited by examiner

Primary Examiner — George Manuel
(74) Attorney, Agent, or Firm — Scott B. Dunbar

(57) ABSTRACT

The present invention is a micro-machined electrode for neural-electronic interfaces which can achieve a ten times lower impedance and higher charge injection limit for a given material and planar area.

20 Claims, 2 Drawing Sheets

HIGH DENSITY ARRAY OF MICRO-MACHINED ELECTRODES FOR NEURAL STIMULATION

CROSS REFERENCE TO RELATED APPLICATIONS

This application is a division of U.S. application Ser. No. 11/488,806, filed Jul. 17, 2006, now U.S. Pat. No. 7,706,893, issued on Apr. 27, 2010, which is a continuation of U.S. application Ser. No. 10/160,468, filed May 1, 2002, now U.S. Pat. No. 7,676,274 B2, issued on Mar. 9, 2010, entitled "High-Density Array of Micro-Machined Electrodes for Neural Stimulation," which claims the benefit of provisional applications 60/287,415, filed May 1, 2001, entitled "High-Density Arrays of Micro-Machined Electrodes for Neural Stimulation Systems," and 60/314,828, filed Aug. 24, 2001, entitled "Micro-Machined Electrodes for High Density Neural Stimulation Systems," the disclosures of which are hereby incorporated by reference.

GOVERNMENT RIGHTS

This invention was made with government support under grant No. R24EY12893-01, awarded by the National Institutes of Health. The government has certain rights in the invention.

FIELD OF THE INVENTION

This application relates to an improved electrode, in particular, and improved electrode for neural stimulation having an increased surface area.

BACKGROUND OF THE INVENTION

Micromachining has been used to produce neural-electronic interfaces for recording neural activity with cortical probe arrays and planar arrays to form individual cells and clusters of cells. Recently, however, new applications that require the stimulation of neural tissue push the performance limits of conventionally produced microelectrodes. One good example is the development of a visual prosthesis. Blind patients with retinits pigmentosa or macular degeneration (i.e., photoreceptors do not function) observe a visual percept induced by the direct electrical stimulation of the retina. Internationally, several efforts are under way to construct a fall visual prosthetic system.

Examples of implantable nerve stimulators that benefit from very small electrodes are U.S. Pat. No. 5,109,844 ("De Juan"), U.S. Pat. No. 5,935,155 ("Humayun"), and U.S. Pat. No. 5,531,774 ("Schulman"). De Juan and Humayun disclose systems for the electrical stimulation of the retina by a retinal electrode array held against the retina. DeJuan describes an epiretinal electrode array. Humuyan describes a system for capturing a video image, transferring the image wirelessly into a living body and applying the image to a retinal electrode array. Schulman discloses a cochlear stimulator for the deaf.

While small electrodes help create a precise signal to stimulate a single nerve or small group of nerves, the ability of an electrode to transfer current is proportional to its surface area. It is further known that electrical signals transfer more efficiently from an edge than from a flat surface. It is, therefore, desirable for an electrode to have a large surface area with many edges.

One technological challenge is the trade off between electrode density and stimulation current. Although the total charge injection required to illicit a visual percept is generally believed to be fixed, the current used is limited by the electrode area when operated at the maximum current density before undesirable and irreversible electrochemical reactions occur. The result is that the electrode size and density in existing retinal prosthetic development efforts are limited.

Therefore, it is advantageous to increase the total surface area of an electrode without increasing the planar surface area. This can only be accomplished by increasing the vertical surface area. One method of increasing surface area is to roughen the surface by rapid electroplating. This is commonly done with platinum electrodes and known as platinum black as described in U.S. Pat. No. 4,240,878 ("Carter"). Platinum black is not very strong and tends to flake off. This is unacceptable in a neural stimulator. The flaking can be limited by ultrasonic vibrations as described in U.S. Pat. No. 4,750,977 ("Marrese"), but not eliminated. A system is needed to create a high surface area electrode which is strong enough for human implantation.

SUMMARY OF THE INVENTION

The present invention is a micro-machined electrode for neural-electronic interfaces which can achieve a ten times lower impedance and higher charge injection limit for a given material and planar area. By micro machining posts or other protuberances on the surface of an electrode, the surface area of the electrode is increased, thus improving the electrical characteristics of the electrode.

BRIEF DESCRIPTION OF THE DRAWINGS

Preferred embodiments demonstrating the various objectives and features of the invention will now be described in conjunction with the following drawings.

DETAILED DESCRIPTION OF THE PREFERRED EMBODIMENTS OF THE INVENTION

Figure 1:
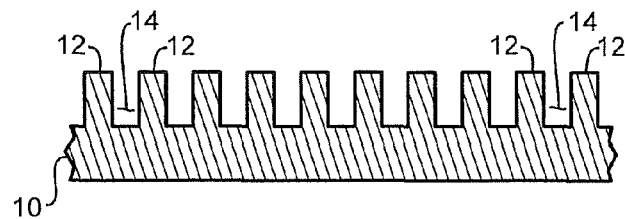
FIG. 1 shows an electrode according to the present invention.

Referring to FIG. 1, the present invention is an electrode with a high aspect ratio surface plated or cut to create maximum surface area within a given planar surface area. The electrode includes a planar base 10, covered with micromachined posts 12 and valleys 14. Alternatively, ridges can be micromachined to increase strength. By making the ridges curved in the horizontal direction strength is increased. While one of skill in the art may think of many possible shapes, any micromachined protuberances are believed to fall within the spirit of the invention. Micromachining techniques can create posts with an aspect ratio of 2 or more. That is, posts which are twice as high as they are wide. Since the area of a surface covered in posts is equal to the horizontal area plus one times the height divided by the width, an increase of surface are by a factor of three is easily obtainable.

Figure 2:
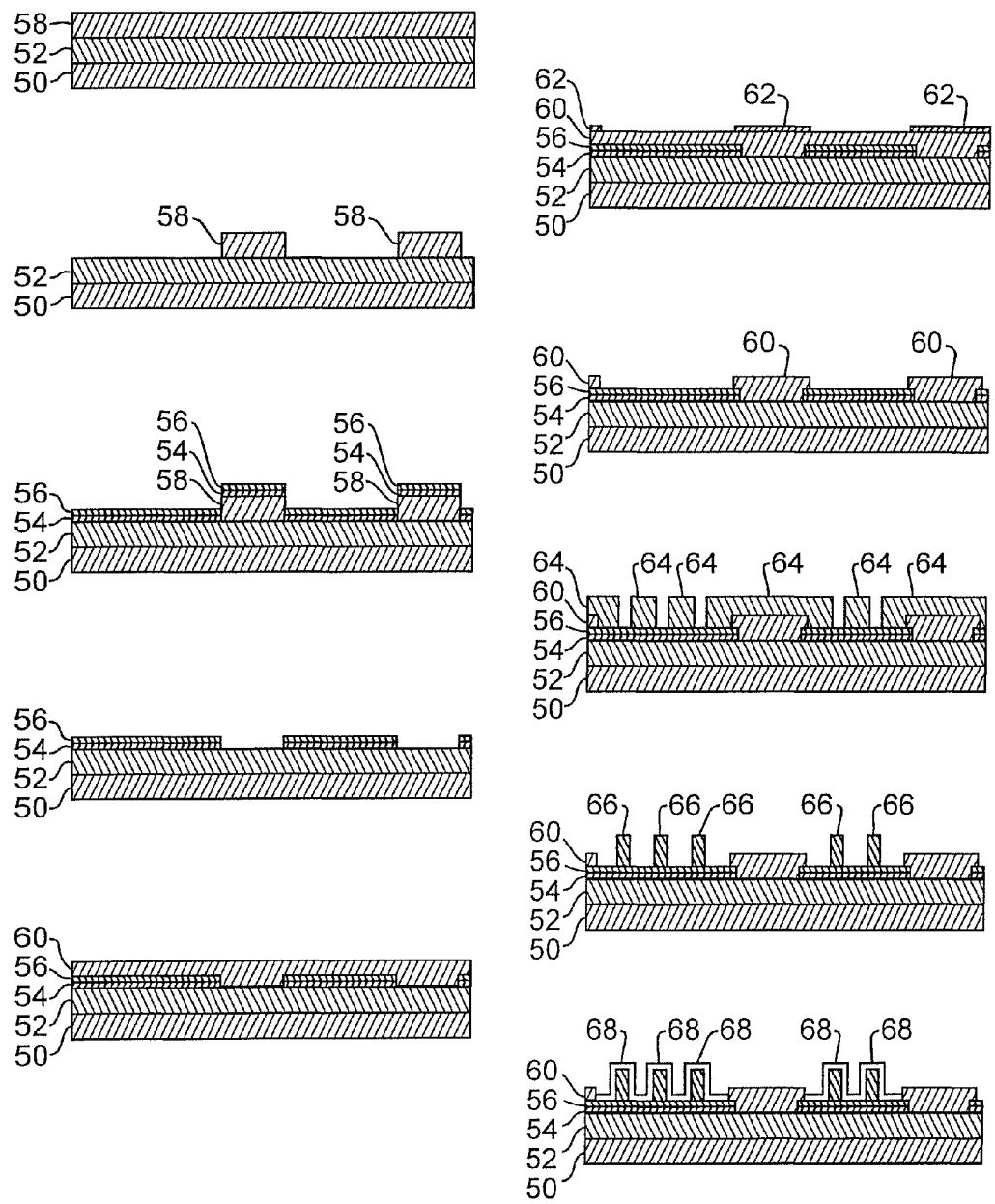
FIG. 2 shows the steps of forming an electrode array according to present invention.

Referring to FIG. 2, the present electrode is formed by techniques similar to that of manufacturing semiconductors. A photoresist layer is applied by photolithographic techniques. Then, an etching acid is used to remove material not protected by the photoresist layer, or material is plated to metals not protected by the photoresist. Electrode arrays according to the present invention can be formed on flexible or rigid substrates. The preferred embodiment is built on a polyimide flexible substrate using titanium and platinum, gold or a combination of platinum and gold. Polyimide is used as a supporting material and for electrical isolation. The fabrication process begins with a silicon wafer, 50, which simply acts as a passive substrate, which is later removed A 5 .mu.m lower polyimide film 52 is deposited to form the lower insulator and base to supply mechanical support for the flexible array. For a rigid substrate, the lower polyimide film 52 may be replaced by silicon dioxide, aluminum oxide, silicon carbide, diamond, or zirconium oxide film, and the silicon wafer 50 is not removed. The electronic base of the electrode array and the interconnect is formed by a 100 nm film of titanium 54, followed by a 100 nm film of platinum 56 deposited by electron-beam evaporation. Titanium adheres better to polyimide than platinum and is provided under the platinum for adhesion purposes. Prior to depositing the metal films 54 and 56 to the polyimide a photoresist layer 58 is patterned on the lower polyimide film 52. A lift-off process that uses STR 1045 photoresist 58 and an acetone soak are used to pattern the metal films 54 and 56. An upper polyimide film 60 is spun on to a thickness of 5 .mu.m and then hard baked at 350.degree. C. to form a structure in which the titanium film 54 and platinum film 56 is sandwiched between two insulating polyimide layers 52 and 60.

The upper polyimide film 60 must be patterned to expose the electrode sites. To accomplish this we first deposit and pattern an aluminum etch mask 62 and then remove all unprotected polyimide in an oxygen/CF.sub.4 gas mix plasma etch.

A 25 .mu.m layer of photoresist 64 is used to define openings for the subsequent electroplating of the high aspect ratio microstructures made of platinum or gold. Platinum or gold posts 66 are plated on to the platinum film 56. If the thickness of the plated platinum posts 66 exceeds 0.5 .mu.m, the high stress in the platinum posts 66 may cause the platinum posts 66 to delaminate from the platinum film 56 or lift up the platinum film 56 from the lower polyimide film 52. Gold structures exhibit better plating characteristics but are less stable under electrical stimulation. Therefore, it is advantageous to plate micro post 66 first with gold and then a with platinum layer 68 over the top of the gold microposts 66.

New platinum plating technologies show promise for overcoming platinum plating problems. If so, it may be useful to first plate platinum posts covered with Iridium or Iridium oxide. Iridium has electrochemical advantages and is even more difficult to plate than platinum. Other materials may also make an effective final layer and may be plated over platinum or gold, these include titanium oxide, rhodium palladium.

If gold is used in microposts 66, it is important that the layer over the gold 68 be hermetic. While the preferred embodiment uses electroplating, other methods are known in the art for making thin hermetic layers such a sputtering, ion-beam deposition, and ion-beam assisted deposition. This methods can also be used for depositing the metal films 54 and 56 on the polyimide film 52. In addition to plating, the microposts 66 may be micromachined by etching or lift off techniques. Once the high aspect ratio structures have been plated, the photoresist plating mask is removed and the electrodes are electrochemically tested. In the final step, the silicon base 50 is removed.

Initially the electrode surfaces consisted of arrays of microposts or the inverse, micromesh. However, due to the stress in the electrodeposits, the much larger structures formed for the mesh electrode geometry was found to be impractical for platinum.

It is possible to cause electrodeposition to occur on the sidewalls of the photoresist plating mold. This yields hollow micropost and further increases the surface area. During the normal developing process, the KOH-based developer removes the exposed regions of the photoresist and then is rinsed away thoroughly. If the rinsing procedure is inadequate, the KOH-based developer is not efficiently diluted, particularly from the sidewalls. Conductivity is high enough to act as a seed layer during electrodeposition. In fact, a cross section of a hollow cylindrical micropost reveals that indeed the thickness of the plated material on the base of the hollow micropost is the same as that grown on the sidewalls of the exposed photoresist. It is also noteworthy that only the sidewalls of the resist become plated and not the top surface of the photoresist. A systematic study of the impact of the rinsing process on sidewall plating showed that when a developed sample is soaked in stagnant water for less than 10 minutes, plating will occur on the photoresist side walls. Longer soaks result in the expected results (i.e., flat plating of the electrode surface up through the plating mold to result in a solid micropost). The sidewall plating process has been found to be reproducible also for the electrodeposition of platinum, gold, and even nickel.

Figure 3:
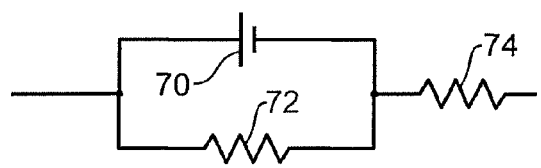
FIG. 3 shows the electrical circuit equivalent of a neural stimulation electrode.
Figure 4:
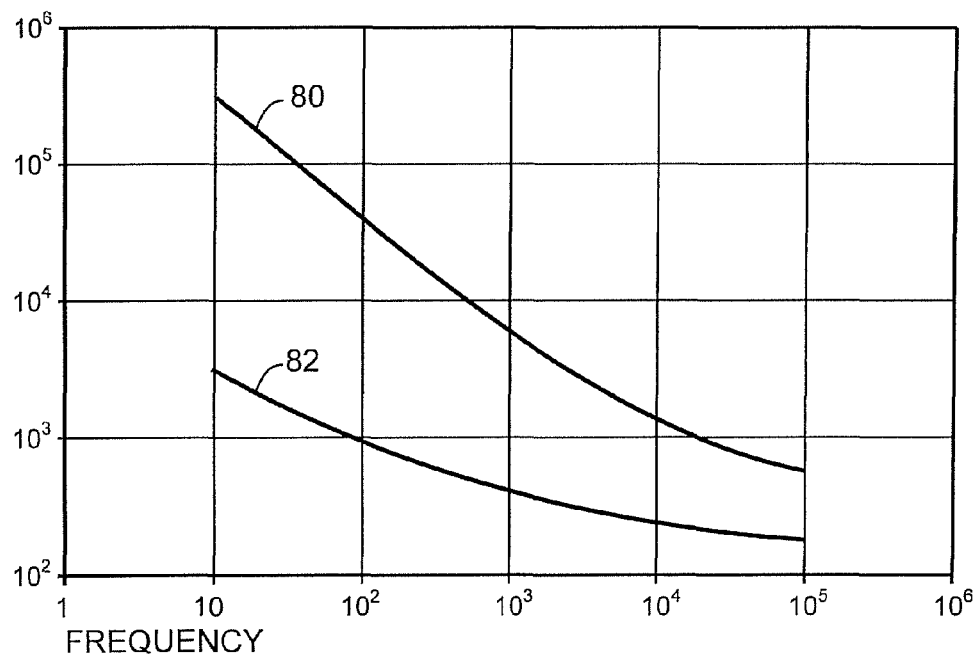
FIG. 4 shows applicant's test results from use of the preferred electrode.

To characterize the electrochemical dependence of electrode area for the flat and micromachined structures an impedance analyzer was used to measure the current induced by the application of a small voltage fluctuation (e.g., 5 mV) as show in FIG. 4. Typically an electrode surface can be modeled (as shown in FIG. 3) with a capacitance 70 and resistance 72 in parallel and a solution resistance 74 in series. The capacitance 70 of the electrode corresponds to the fast charge build up across the electrode electrolyte interface when voltage is applied. The electrode-electrolyte resistance 72 describes the lower faradic conductance of charge transfer by means of chemical reaction between solution and the electrode metal. The solution resistance 74 represents the resistance of the solution.

The capacitance 70 and resistance 72 values typically vary widely with voltage, time, and concentration, and are challenging to model precisely. However, because our experiment setup employs small alternating voltage fluctuations, resistance 70, capacitance 72 and solution resistance 74, can be approximated by simple linear values over the small voltage range. Since capacitance 70 is proportional to surface area and resistance 72 is inversely dependent on area, the resulting parallel conductance is also directly proportional to surface area.

Thus proportionality between conductance and surface area is observed in our experimental impedance measurements. From the impedance curve of each electrode sample (FIG. 4) the value is taken at 1 kHz and plotted against the estimated surface area. A flat electrode curve 80 shows the impedance of a flat electrode at various frequencies. A micromachined electrode curve 82 shows lower impedance for the micromachined electrode, with a greater improvement at lower frequencies. For structures with an aspect ratio of height divided by width equal to 1, doubling of the effective electrode impedance is expected and observed. However, when the aspect ratio is increased further to realize a larger surface area, experimental results show that improvement in conductance advantage plateaus at a 4.times. increase in physical surface area. Since the plateau can be overcome to obtain larger increases in conductance with surface area, the measured conductance is limited by the solution resistance 74 in the high-aspect ratio features.

The above detailed description is provided to illustrate the specific embodiments of the present invention and is not intended to be limiting. Numerous variations and modifications are possible within the scope of the present invention. The present invention is defined by the following claims.

We claim:

1. A single electrode with enhanced surface area comprising:
   a single electrode base having a conductive surface with a planar surface area; and
   a plurality of micromachined conductive protuberance on said surface of said single electrode base; wherein a physical surface area of said single electrode base results in a reduction in the electrode impedance at low frequencies relative to said planar surface area.

2. The electrode according to claim 1, wherein said protuberances are posts.

3. The electrode according to claim 2, wherein said posts are hollow posts.

4. The electrode according to claim 1, wherein said protuberances are ridges.

5. The electrode according to claim 1, wherein said protuberances comprise platinum.

6. The electrode according to claim 1, wherein said protuberances comprise gold.

7. The electrode according to claim 1, wherein said protuberances comprise gold covered with platinum.

8. The electrode according to claim 1, wherein said protuberances comprise iridium.

9. The electrode according to claim 1, wherein said protuberances comprise iridium oxide.

10. The electrode according to claim 1, wherein said protuberances comprise titanium oxide.

11. The electrode according to claim 1, wherein said protuberances comprise a first metal and a second metal forming a hermetic seal over said first metal.

12. An electrode array comprising:
    a lower flexible insulating layer;
    a flexible conductive layer;
    an upper flexible insulating layer including voids exposing a portion of said flexible conductive layer having a conductive surface with a planar surface area; and
    a plurality of micromachined conductive protuberance on said surface.

13. The electrode array according to claim 12, wherein at least one of said flexible insulating layers comprises polyimide.

14. The electrode array according to claim 12, wherein said flexible conductive layer comprises platinum.

15. The electrode array according to claim 12, wherein said flexible conductive layer comprises titanium.

16. The electrode array according to claim 12, wherein said protuberances comprise gold.

17. The electrode array according to claim 12, wherein said protuberances are posts.

18. The electrode array according to claim 17, wherein said post are hollow posts.

19. The electrode array according to claim 12, wherein said protuberances are ridges.

20. A method of increasing an electrode effective surface area of a single electrode comprising the steps of:
    providing a single conductive electrode base having a planar surface area; and
    micromachining a plurality of conductive protuberances on the surface of said single electrode base; said plurality of protuberances comprising a first metal and a second metal covering said first metal; wherein said physical surface area of said single electrode results in a reduction in the electrode impedance at low frequencies relative to the single electrode base planar surface area.

* * * * *